United States Patent [19]

Shepard et al.

[11] Patent Number: 4,721,794
[45] Date of Patent: Jan. 26, 1988

[54] SUBSTITUTED THIOPHENE-2-SULFONAMIDE ANTIGLAUCOMA AGENTS

[75] Inventors: Kenneth L. Shepard, North Wales; Samuel L. Graham, Harleysville, both of Pa.

[73] Assignee: Merck & Co., Inc., Rahway, N.J.

[21] Appl. No.: 890,576

[22] Filed: Jul. 30, 1986

Related U.S. Application Data

[63] Continuation of Ser. No. 667,666, Nov. 2, 1984, abandoned.

[51] Int. Cl.$^4$ .................. C07D 333/22; C07D 241/04; C07D 265/30
[52] U.S. Cl. ...................................... 549/65; 514/315; 514/326; 514/351; 514/396; 514/401; 514/408; 514/445; 544/146; 544/379; 546/184; 546/284; 546/347; 548/327; 549/60; 549/61; 549/66
[58] Field of Search ..................... 549/60, 61, 65, 66; 546/184, 284, 347; 544/327, 146, 379; 548/354, 347, 527; 514/227, 238, 255, 276, 315, 326, 351, 396, 401, 408, 445

[56] References Cited

FOREIGN PATENT DOCUMENTS 0042731 12/1981 European Pat. Off. ............... 549/65
1459571 12/1976 United Kingdom .................. 549/65

OTHER PUBLICATIONS

Barnish et al., C.A., vol. 90, 1979, 90:54813u, p. 598.
Cross et al., C.A., vol. 87, 1977, 87:84803w, p. 579

Primary Examiner—Henry R. Jiles
Assistant Examiner—J. G. Mullins
Attorney, Agent, or Firm—William H. Nicholson; Michael C. Sudol

[57] ABSTRACT

Thiophene-2-sulfonamides with a 5-alkyl-$S(O)_n$-substituent are carbonic anhydrase inhibitors useful in the treatment of elevated intraocular pressure.

5 Claims, No Drawings

SUBSTITUTED THIOPHENE-2-SULFONAMIDE ANTIGLAUCOMA AGENTS

This is a continuation of application Ser. No. 667,666, filed Nov. 2, 1984, now abandoned.

SUMMARY OF THE INVENTION

This invention relates to novel thiophene-2-sulfonamides useful in the treatment of elevated intraocular pressure. More particularly this invention relates to compounds having the structural formula:

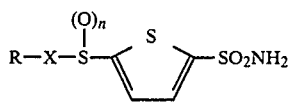

wherein R, X and n are hereinafter defined, as well as the pharmaceutically and ophthalmologically acceptable salts thereof. This invention also relates to pharmaceutical compositions and the use thereof for systemic and ophthalmic use employing a novel compound of this invention as active ingredient for the treatment of elevated intraocular pressure, especially when accompanied by pathological damage such as in the disease known as glaucoma.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that render them unacceptable for chronic ocular use. (S)-1-tert-Butylamino-3-[(4-morpholino-1,2,5-thiadiazol-3-yl)oxy]-2-propanol, β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof.

To be an effective and acceptable topical agent, an ophthalmic carbonic anhydrase inhibitor must not only penetrate the ophthalmic tissues to reach the active sites within the eye, but it must also be devoid of those side effects including irritation, allergic reaction and the like which would militate against long term administration.

DETAILED DESCRIPTION OF THE INVENTION

The novel compounds of this invention have structural formula:

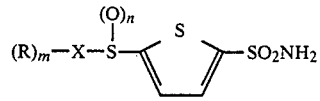

or a pharmaceutically acceptable salt thereof, wherein
X is a straight, branched or cyclic, saturated or unsaturated hydrocarbon of up to 10 carbon atoms, such as

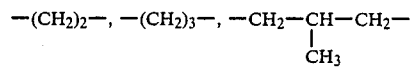

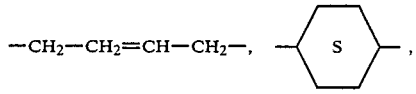

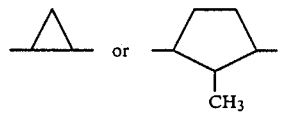

m is 1 or 2;
n is 0, 1 or 2;
R is
(1) —OR$^1$ wherein R$^1$ is
 (a) hydrogen,
 (b) C$_{1-4}$ alkyl,
 (c) hydroxy-C$_{1-4}$ alkyl,
 (d) C$_{1-4}$ alkoxy-C$_{1-4}$ alkyl,
 (e) phenyl,
 (f) pyridyl
 (g) carboxy-C$_{1-4}$ alkyl,
 (h) ω-amino-ωcarboxy-C$_{1-4}$ alkyl;

(2)

(3)

(4) 

(5) 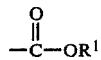

(6) 

(7) —N(R¹)₂ wherein the R¹ groups are the same or different, or can be joined together to form, with the nitrogen atom to which they are attached, a 5-or 6-membered heterocycle such as piperidino, piperazino, morpholino, 1-pyrrolyl, or the like.

(8) 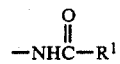

(9) 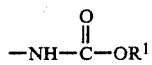

(10) phenyl, either unsubstituted or substituted with one or more of
 (a) hydroxy,
 (b) $C_{1-4}$ alkoxy,
 (c) $C_{1-5}$ alkanoyloxy,
 (d) halo, such as chloro or bromo,
 (e) $C_{1-4}$ alkyl,
 (f) —NR²R³, wherein R² and R³ are independently,
  (i) hydrogen,
  (ii) alkyl, or
  (iii) $C_{1-5}$ alkanoyl,

(11) 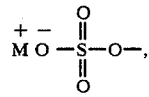

wherein M⁺ is an ophthalmologically acceptable cation selected from sodium, potassium ammonium, tetra ($C_{1-4}$alkyl)ammonium, pyridinium, imidazolium, pralidoxime, and thiamine

(12) 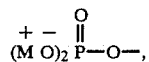

wherein M³⁰ is as previously defined;

(13) 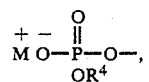

wherein R⁴ is —$C_{1-3}$ alkyl OR⁴ or phenyl —$C_{1-3}$ alkyl; or

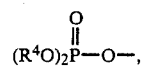

wherein R⁴ is as previously defined, and the two may be the same or different.

It is preferred that n=2, i.e. that the 5-substituent be a sulfone moiety. It is further preferred that X be —(CH₂)₁₋₄—, and if R is phenyl or substituted phenyl it is preferred that X be —CH₂—(methylene).

Specific compounds within the scope of this invention are:
5-(4-methoxybenzylthio)thiophene-2-sulfonamide
5-(4-hydroxybenzylthio)thiophene-2-sulfonamide
5-(4-methoxybenzylsulfonyl)thiophene-2-sulfonamide
5-(4-hydroxybenzylsulfonyl)thiophene-2-sulfonamide
5-(2-hydroxyethylthio)thiophene-2-sulfonamide
5-(2-hydroxyethylsulfonyl)thiophene-2-sulfonamide
5-(2,3-dihydroxypropylthio)thiophene-2-sulfonamide
5-(2,3-dihydroxypropylsulfonyl)thiophene-2-sulfonamide
5-(trans-4-hydroxycyclohexylthio)thiophene-2-sulfonamide
5-(trans-4-hydroxycyclohexylsulfonyl))thiophene-2-sulfonamide
5-(2-acetoxyethylsulfonyl)thiophene-2-sulfonamide
5-(3-hydroxypropylsulfonyl)thiophene-2-sulfonamide
5-(3-hydroxypropylthio)thiophene-2-sulfonamide The novel process of this invention comprises as the principal step the condensation reaction of a 5-halo-1-sulfamoylthiophene with a mercaptan of formula R—X—SH under the influence of a strong base. The reaction may be illustrated as follows:

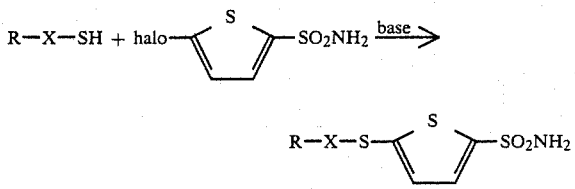

wherein halo is chloro, bromo or iodo, preferably bromo.

The thiophene starting material is represented above as a thiophene sulfonamide and is a quite useful reagent. However, the reaction is usually cleaner and better yields are achieved if the sulfonamide group is protected by an easily removed protecting group such as the N,N-dimethylformamidine. In other words, the starting material might actually be of structure:

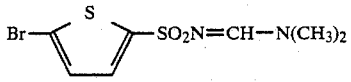

The formamidine protecting group is readily removed by treatment with a mineral acid or aqueous base.

In the novel process, the mercaptan, the halothiophene and strong base in approximately equimolar amounts are admixed in a polar organic solvent such as dimethyl formamide, hexamethylphosphoramide, dimethylsulfoxide, or the like and stirred at about 10° C. to 100° C. for about 0.5 to 3 hours. The preferred laboratory technique is to treat the mercaptan with the strong base at about 10° C. to 30° C. followed by addition of the halothiophene with aging at about 10° C. to 100° C. for the requisite time period. Strong bases suitable for use in the novel process include alkali metal hydrides and alkoxides such as sodium, or potassium hydrides, methoxides, ethoxides, isopropoxides, or t-butoxides.

The sulfides produced by the foregoing process are converted to the corresponding sulfones by oxidation with hydrogen peroxide or a peracid such as m-chloroperbenzoic acid or Oxone® (a Dupont trade name for potassuim hydrogen monoperoxysulfate). Oxidation with hydrogen peroxide is conducted in a carboxylic acid medium such as acetic or propionic acid at about 50° to 100° C. for about 0.5 to 8 hours. The oxidation with a peracid is conducted in an inert organic solvent such as ethyl acetate, methanol, ethanol, butyl acetate, or isopropanol at about 10 to about 40° C. for about 1 to 24 hours. Clearly the time is not critical and times longer than that necessary to complete the reaction are not detrimental.

Another process to prepare those compounds wherein R is

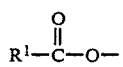

is represented by the following reaction scheme:

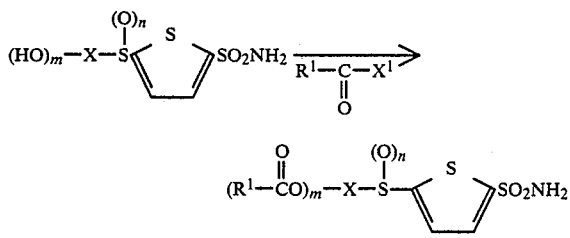

where $R^1$ has the meanings hereinbefore designated, is chloro, bromo, iodo,

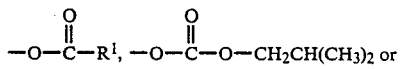  or

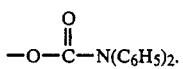.

Generally equimolar amounts of the thiophene and

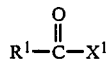

are employed, although use of an excess of the more readily available reactant is satisfactory.

The reaction is conducted in a suitable, inert solvent such as acetone, dimethylformamide, pyridine, ethyl acetate, tetrahydrofuran or benzene and the like with at least an equimolar amount of a hydrohalide acceptor when the acylating agent is an acyl halide or with a carboxylic acid acceptor when the acylating agent is an acid anhydride. Bases such as triethylamine, pyridine and the like may be employed for this purpose.

The reaction may be conducted with or without a catalyst at temperatures of from 0° C. to the boiling point of the solvent used but preferably from about 15° C. to 50° C.

When a catalyst is employed, a 4,4-dialkylaminopyridine such as 4-dimethylaminopyridine or 4-pyrrolidinopyridine is preferred.

The compounds wherein R is

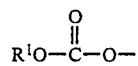

of this invention are most suitably prepared by reacting a compound

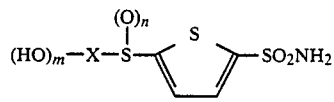

with an appropriate haloformate, particularly a chloroformate of the formula:

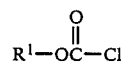

or a bis carbonate of the formula:

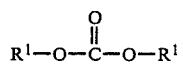

The reaction is conducted in a suitable solvent such as dimethylformamide, pyridine, acetone, ethyl acetate, tetrahydrofuran or benzene and the like with at least an equimolar amount of a hydrohalide acceptor. Bases such as triethylamine, pyridine and the like may be employed for this purpose.

The reaction may be conducted with or without a catalyst at temperatures of from 0° C. to the boiling point of the solvent used but preferably from 15° C. to 50° C.

When a catalyst is employed, triethylamine or a 4,4-dialkylaminopyridine such as 4-dimethylaminopyridine or 4-pyrrolidinopyridine is preferred.

Another process of this invention for preparing the ethers, i.e. $R = OR^1$ wherein $R^1 = H$, the hydroxy compound is treated with an "alkylating" agent of formula $R^1—X^2$ wherein $X^2$ is a halide such as chloride, bromide or iodide, or other good leaving group such as mesylate, tosylate or benzenesulfonate in a suitable solvent such as dimethylformamide, hexamethylphosphoramide, or the like in the presence of a base such as an alkali metal alkoxide, preferably sodium methoxide, at about 0° C. to 35° C., usually about room temperature for about 10 to 30 hours.

The O-sulfates of this invention are prepared by reacting an hydroxyalkylsulfonylthiophene-2-sulfonamide with sulfamic acid in pyridine at elevated temperatures (about 50° C. to the boiling point) for about 18 to 48 hours to provide the ammonium salt followed, if desired, by titration with hydroxides of the formula MOH to provide the other salts.

Similarly the O-phosphates of this invention are prepared by treatment of a hydroxy compound with phosphorus oxychloride, an alkyl dichlorophosphate or a dialkyl chlorophosphate in pyridine or similar basic solvent at about −5° to +5° C. for about 0.25 to 1.0 hour.

In any of the foregoing syntheses the sulfonamide group may be protected as an N,N-disubstituted formamide prepared and removed as described earlier.

The novel pharmaceutical formulations of this invention include formulations for systemic administration and ophthalmic formulations designed for topical ocular administration, preferably the latter.

The formulations for systemic administration comprise a non-toxic pharmaceutically acceptable carrier and an effective amount of one or more of the novel compounds of this invention. They may be in a form (a) for oral administration; e.g., as tablets, in combination with other compounding ingredients customarily used such as talc, vegetable oils, polyols, benzyl alcohols, gums, gelatin, starches and other carriers; dissolved or dispersed or emulsified in a suitable liquid carrier; in hard or soft capsules, encapsulated in a suitable material; or (b) for parenteral administration; e.g., dissolved or dispersed in a suitable liquid carrier as a solution, suspension or emulsion, or (c) for transdermal application, e.g. as a patch.

The active drugs of this invention are most suitably administered in the form of ophthalmic pharmaceutical compositions adapted for topical administration to the eye such as a solution, suspension, ointment, or as a solid insert. Formulations of these compounds may contain from 0.01 to 15% and especially 0.5% to 2% of medicament. They may contain a novel compound of this invention as the sole medicament or may contain as well an effective amount of a β-adrenergic blocking agent such as timolol maleate or a parasympathomimetic agent such as pilocarpine. The two active principles are present in approximately equal amounts on a weight basis.

The pharmaceutical preparation which contains the active compound may be conveniently admixed with a non-toxic pharmaceutical inorganic or organic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may also be in the form of a solid insert such as one which after dispensing the drug remains essentially intact, or a bio-erodible insert that either is soluble in lacrimal fluids, or otherwise disintegrates.

Generally, doses of the present compounds of about 0.01 to about 50 mg/kg and preferably from about 0.1 to about 20 mg/kg of body weight per day may be used. Dosage may be single or multiple depending on the daily total required and the unit dosage.

EXAMPLE 1

5-(4-Methoxybenzylthio)thiophene-2-sulfonamide

Step A:

Preparation of N,N-Dimethyl-N'-(5-bromothiophene-2-sulfonyl)formamidine

To a stirred mixture of 5-bromothiophene-2-sulfonamide (24.2 g, 0.10 mol) in acetonitrile (100 ml) was added dimethylformamide dimethyl acetal (14 ml) in acetonitrile (125 ml) dropwise over 0.5 hour. After an additional 0.5 hour the solvent was removed in vacuo. The residue was treated with water and the solid that precipitated was collected and dried, 28.7 g., m.p. 103°–105° C. Recrystallization from 1-chlorobutane gave material with m.p. 104°–106° C.

Anal. Calc'd. for $C_7H_9BrN_2O_2S_2$ (297.21): C, 28.29; H, 3.05; N, 9.43. Found: C, 28.07; H, 3.03; N, 9.53.

Step B:

Preparation of N,N-Dimethyl-N'-[5-(4-methoxybenzylthio)thiophene-2-sulfonyl]formamidine A solution of 4-methoxy-α-toluenethiol (7.7 g, 0.05 mol) in DMF (10 ml) was added dropwise to a stirred mixture of sodium hydride (2.50 g, 50% oil dispersion, 0.054 mol) in DMF (40 ml). When gas evolution was complete, N,N-dimethyl-N'-(5-bromothiophene-2-sulfonyl)formamidine (14.85 g; 0.05 mol) was added and the resulting mixture was stirred for 1 hour at 25° C. The reaction mixture was diluted with water and the solid that separated was collected, washed with water and dried to give 15.36 g., m.p. 92°–101° C. Recrystallization from 1-chlorobutane gave material with m.p. 110°–111.5° C.

Anal. Calc'd. for $C_{15}H_{18}N_2O_3S_3$ (370.51): C, 48.62; H, 4.90; N, 7.56. Found: C, 48.98; H, 5.03; N, 7.66.

Step C:

Preparation of 5-(4-Methoxybenzylthio)thiophene-2-sulfonamide

A mixture of N,N-dimethyl-N,N'-[5-(4-methoxybenzylthio)thiophene-2-sulfonyl]formamidine (30.8 g) and 6N hydrochloric acid (500 ml) was heated on the steam bath with stirring for 18 hours. The reaction mixture was diluted with water (1L) and chilled. The resulting solid was collected, washed with water and dried to yield 26 g. Recrystallization from toluene followed by dichloroethane gave material with m.p. 139°–141° C.

Anal. Calc'd. for $C_{12}H_{13}NO_3S_3$ (315.43): C, 45.69; H, 4.15; N, 4.44. Found: C, 45.96; H, 4.10; N, 4.62.

Employing the procedure substantially as described in Example 1, but substituting for the 4-methoxy-α-toluenethiol used in Step B the thiols of formula R—X—SH described in Table I there are produced the substituted thiophene-2-sulfonamides, also described in Table I in accordance with the following reaction scheme.

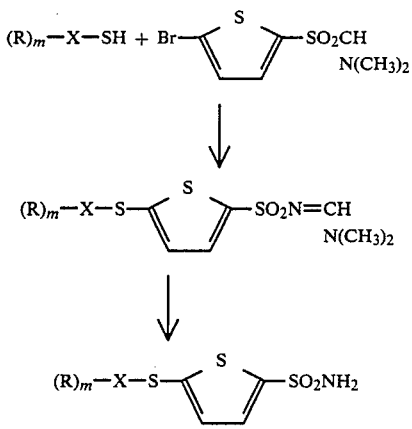

TABLE I

| R | m | X |
|---|---|---|
| 3-Cl-C6H4- | 1 | —CH2— |
| 3-Cl-4-CH3-C6H3- | 1 | —CH2— |
| 4-(CH3)2N-C6H4- | 1 | —CH2— |
| 4-CH3(H)N-C6H4- | 1 | —CH2— |

EXAMPLE 2

5-(4-Hydroxybenzylthio)thiophene-2-sulfonamide

A solution of boron tribromide (3.12 ml, 8.27g, 0.033 mol) in methylene chloride (30 ml) was added dropwise to a stirred solution of 5-(4-methoxybenzylthio)thiophene-2-sulfonamide (3.4 g, 0.11 mol) in methylene chloride (100 ml). The dark reaction mixture was stirred four hours, treated with water (125 ml) and extracted with ethyl acetate (500 ml). The organic layer was separated, washed with water (2×100 ml), saturated NaCl solution (100 ml) and dried (Na2SO4). The filtrate was evaporated to dryness, the residue slurried with ether and filtered to give 0.95 g off-white solid. Recrystallization from dichloroethane gave material with m.p., 167°–168.5° C.

Anal. Calc'd. for $C_{11}H_{11}NO_3S_3$ (301.41): C, 43.83; H, 3.68; N, 4.65. Found: C, 43.67; H, 3.62; N, 4.69.

EXAMPLE 3

5-(4-Methoxybenzylsulfonyl)thiophene-2-sulfonamide

A mixture of 5-(4-methoxybenzylthio)thiophene-2-sulfonamide (6.5 g) and 30 % hydrogen peroxide (6.5 ml) in acetic acid (65 ml) was heated on the steam bath for 1 hour. The reaction mixture was diluted with water (400 ml) and the solid that separated was collected and dried, 4.52 g, m.p. 198°–203° C. Recrystallization from 2-propanol gave material with m.p. 204°–206° C.

Anal. Calc'd. for $C_{12}H_{13}NO_5S_3$ (347.43): C, 41.48; H, 3.77; N, 4.03. Found: C, 41.37; H, 3.66; N, 3.86.

Employing the procedure substantially as described in Example 3, but substituting for the 5-(4-methoxybenzylthio)thiophene-2-sulfonamide an equimolar amount of the benzylthio compounds described in Table II, there are produced the benzylsulfonyl compounds also described in Table II in accordance with the following reaction scheme:

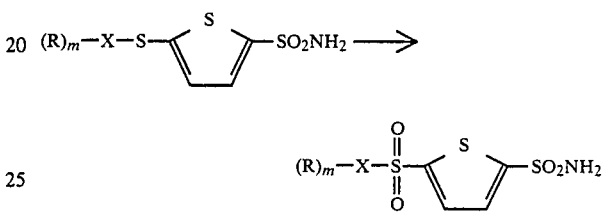

TABLE II

| (R) | m | X |
|---|---|---|
| 3-Cl-C6H4- | 1 | —CH2— |
| 3-Cl-4-CH3-C6H3- | 1 | —CH2— |
| 4-(CH3)2N-C6H4- | 1 | —CH2— |
| 4-CH3(H)N-C6H4- | 1 | —CH2— |

EXAMPLE 4

5-(4-Hydroxybenzylsulfonyl) thiophene-2-sulfonamide m-Chloroperoxylbenzoic acid (1.29 g, 80–85% pure, about 6 mmols) was added in one portion to a stirred solution of 5-(4-hydroxybenzylthio) thiophene-2-sulfonamide (0.86 g, 2.9 mmols) in ethyl acetate (10 ml) and methanol (2 ml). After two hours at ambient temperature, the mixture was diluted with 25 ml of ether and filtered to give 0.50 g off-white solid, m.p. 220°–222° C. (dec.).

Anal. Calc'd. for $C_{11}H_{11}NO_5S_3$ (333.41): C, 39.62; H, 3.33; N, 4.20. Found: C, 39.56; H, 3.10; N, 4.12.

EXAMPLE 5

5-(2-Hydroxyethylthio)thiophene-2-sulfonamide

Step A:

Preparation of N,N-Dimethyl-N'-5[(2-hydroxyethylthio)thiophene-2-sulfonyl]formamidine A solution of 2-mercaptoethanol (5.85 g, 0.075 mol) in DMF (10 ml) was added dropwise to a stirred mixture of sodium hydride (3.45g, 0.075 mol, 50% oil) in DMF (50 ml). When gas evolution was complete, N,N-dimethyl-N,N'-(5-bromothiophene-2-sulfonyl)formamidine (14.85 g, 0.05 mol) was added and the mixture was heated to 80° C. for 1.5 hours. The reaction mixture was diluted with ice cold water (400 ml), extracted with petroleum ether to remove mineral oil then with ethyl acetate (3×300 ml). The ethyl acetate extracts were washed with saturated brine, filtered through sodium sulfate and evaporated in vacuo to give 2.8 g of product as a light brown oil.

Step B:

5-(2-Hydroxyethylthio)thiophene-2-sulfonamide

The crude product from Step A was dissolved in methanol (50 ml), 10% aqueous sodium hydroxide (50 ml) was added and the solution was heated on the steam bath for 1.5 hours. The methanol was removed under reduced pressure, the residue diluted with water, acidified with 6N hydrochloric acid and extracted with ethyl acetate (3×250 ml). The residue after evaporation of the ethyl acetate was chromatographed over silica gel eluting with a 5%–7.5% methanol in chloroform (v/v) gradient. The fractions containing the desired product were pooled and evaporated to an oil that solidified after being subjected to vacuum for 24 hours. This material was crystallized from ether-petroleum ether after storage at −20° C., m.p. 46.5–47.5° C.

Anal. Calcd. for $C_6H_9NO_3S_3$ (239.34): C, 30.11; H, 3.79; N, 5.58. Found: C, 30.37; H, 3.74; N, 5.66.

EXAMPLE 6

5-(2,3-Dihydroxypropylthio)thiophene-2-sulfonamide

A solution of 2,3-dihydroxypropanethiol (8.11 g, 0.075 mol) in DMF (10 ml) was added dropwise to a stirred mixture of NaH (3.45 g, 50% oil, 0.075 mol) and DMF (40 ml) under nitrogen. When gas evolution was complete, a solution of N,N-dimethyl-N'-(5-bromothiophene-2-sulfonyl)formamidine (14.85 g, 0.05 mol) in DMF (50 ml) was added rapidly and the resulting mixture was heated on the steam bath for one hour. After an additional 16 hours at ambient temperature, the reaction mixture was diluted with water (500 ml) and extracted with ethyl acetate (250 ml). Sodium hydroxide (100 g) was added to the aqueous layer and this solution warmed on the steam bath for two hours. After cooling to ambient temperature, the mixture was filtered and the clear filtrate was acidified with concentrated HCl. The solution was extracted with ethyl acetate (3×300 ml), the extracts were washed with saturated NaCl and dried (Na₂SO₄) Filtration and evaporation of the solvent left the product as a light amber oil, 13.3 g.

EXAMPLE 7

5-(trans-4-Hydroxycyclohexylthio)thiophene-2-sulfonamide

Trans-4-Hydroxycyclohexylmercaptan (9.92 g, 0.075 mol) in DMF (10 ml) was added dropwise to a stirred mixture of NaH (3.45 g, 50 % oil, 0.075 mol) and DMF (40 ml). When gas evolution was complete, N,N-dimethyl-N'-(5-bromothiophene-2-sulfonyl)formamidine (14.85 g, 0.05 mol) was added in one portion, rinsed in with DMF (10 ml) and the resulting mixture was heated on the steam bath for 1 hour. The DMF was removed under reduced pressure and the residue was stirred with methanol (50 ml) and 10% sodium hydroxide solution (50 ml) overnight. The methanol was evaporated and the resulting aqueous solution was added to 10% HCl (400 ml) and chilled. The solid that separated was collected and washed with water. The residue was triturated with 1-chlorobutane to give a solid, (12.0 g) after drying. Recrystallization from water followed by dichloroethane gave material with m.p. 145°–147° C.

Anal. Calc'd. for $C_{10}H_{15}NO_3S_3$ (293.248): C, 40.93; H, 5.15; N, 4.77. Found: C, 41.14; H, 5.15; N, 4.57.

EXAMPLE 8

5-(3-Hydroxypropylthio)thiophene-2-sulfonamide

Employing the procedure substantially as described in Example 5, but substituting for the 2-mercaptoethanol used in Step A thereof an equimolar amount of 3-mercaptopropanol, there are produced in sequence:

Step A: N,N-dimethyl-N'-5-[(3-hydroxypropylthio)-thiophene-2-sulfonyl]-formamidine; and Step B: 5-(3-hydroxypropylthio)thiophene-2-sulfonamide, m.p. 62°–63.5° C.

Employing a procedure substantially as described in Examples 5, 6, 7 or 8 but substituting for the mercaptans employed therein, the mercaptans described in Table III, there are produced the substituted thiophenes also described in Table III in accordance with the following reaction scheme:

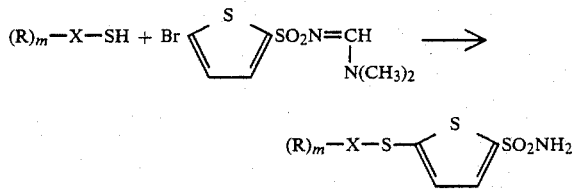

TABLE III

| R | m | X |
|---|---|---|
| HO(CH₂)₂O— | 1 | —(CH₂)₂— |
| CH₃O(CH₂)₂O— | 1 | —(CH₂)₃— |
| CH₃(CH₂)₃O— | 1 | —(CH₂)₂— |
| C₆H₅—O— | 1 | —(CH₂)₃— |
| HO— | 1 | CH₃<br>\|<br>—C—CH₂CH₂—<br>\|<br>CH₃ |

TABLE III-continued

| R | m | X |
|---|---|---|
| ![pyridyloxy] N⟨⟩−O− | 1 | −(CH₂)₂− |
| HOOC−CH₂CH₂O− | 1 | −(CH₂)₃− |
| HOOC−CH−CH₂O−<br>\|<br>NH₂ | 1 | −(CH₂)₃− |
| (CH₃)₂N− | 1 | −(CH₂)₄− |

EXAMPLE 9

5-(2-Hydroxyethylsulfonyl)thiophene-2-sulfonamide

A solution of 5-(2-hydroxyethylthio)thiophene-2-sulfonamide (12.8 g) in glacial acetic acid (90 ml) and 30% hydrogen peroxide (20 ml) was warmed on the steam bath for one hour. The reaction mixture was diluted with ice water (600 ml) and extracted with ethyl acetate (3×250 ml). The combined extracts were washed with saturated NaHSO₃, saturated NaCl and dried (Na₂SO₄). After filtration and removal of the solvent, the residue (8.5 g) was chromatographed over silica gel (100 g) with chloroform-methanol (9:1, v/v) as the eluant. The fractions containing the desired product were combined and stripped to 3.6 g of solid product.

Anal. Calc'd. for $C_6H_9NO_5S_3$ (271.34): C, 26.56; H, 3.34; N, 5.16. Found: C, 26.64; H, 3.42; N, 5.31.

EXAMPLE 10

5(2,3-dihydroxypropylsulfonyl)thiophene-2-sulfonamide

A solution of m-chloroperoxybenzoic acid (4.3 g, 80–85%, about 0.02 mols) in ethyl acetate (25 ml) was added dropwise to a stirred solution of the product from Example 6 (2.7 g, 0.01 mol) in methanol (25 ml). The resulting clear solution was stirred overnight and the solvent removed in vacuo. The white solid residue was slurried with ether, filtered and the solid dried on the filter, 2.0 g. Recrystallization from ethyl acetate gave material with m.p., 128°–131° C.

Anal. Calc'd. for $C_7H_{11}NO_6S_3$ (301.37): C, 27.90; H, 3.68; N, 4.65. Found: C, 27.94; H, 3.65; N, 4.66.

EXAMPLE 11

5-(3-Hydroxypropanesulfonyl)thiophene-2-sulfonamide

Employing the procedure substantially as described in Example 9, but substituting for the 5-(2-hydroxyethylthio)thiophene-2-sulfonamide used therein, an equimolar amount of 5-(3-hydroxypropylthio)thiophene-2-sulfonamide, there is produced 5-(3-hydroxypropanesulfonyl)thiophene-2-sulfonamide; m.p. 106.5°–108° C.

EXAMPLE 12

Employing the procedure substantially as described in Example 10, but substituting for the 5-(2,3-dihydroxypropylthio)thiophene-2-sulfonamide used therein, an equimolar amount of 5-(trans-4-hydroxycyclohexylthio)thiophene-2-sulfonamide from Example 7, there is produced in similar yield, 5(trans-4-hydroxycyclohexylsulfonyl) thiopene-2-sulufonamide, m.p. 192–193.5? C.

Employing the procedures substantially as described in Examples 9, 10, 11 or 12 but substituting for the thio compounds used as starting materials therein, the thio compounds described in Table IV, there are produced the corresponding sulfonyl compounds, also described in Table IV in accordance with the following reaction scheme:

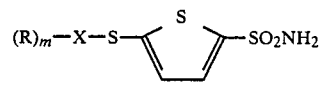

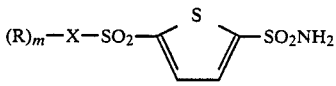

TABLE IV

| R | m | X |
|---|---|---|
| HO(CH₂)₂O− | 1 | −(CH₂)₂− |
| CH₃O(CH₂)₂O− | 1 | −(CH₂)₃− |
| CH₃(CH₂)₃O− | 1 | −(CH₂)₂− |
| ⟨phenyl⟩−O− | 1 | −(CH₂)₃− |
| N⟨⟩−O− | 1 | −(CH₂)₃− |
| HOOC−CH₂CH₂O− | 1 | −(CH₂)₃− |
| HO | 1 | CH₃<br>\|<br>−C−CH₂CH₂<br>\|<br>CH₃ |
| HOOC−CH−CH₂O−<br>\|<br>NH₂ | 1 | −(CH₂)₃− |
| (CH₃)₂N− | 1 | −(CH₂)₄− |

EXAMPLE 13

5-(3-acetyloxypropanesulfonyl)thiophene-2-sulfonamide

To a solution of 5-(3-hydroxypropanesulfonyl)thiophene-2-sulfonamide (1.2 g, 4.2 mmol) in 75 ml of THF was added 0.5 ml of pyridine and 0.5 ml of acetyl chloride. The reaction mixture was stirred for 18 hours at room temperature. The reaction mixture was filtered and the filtrate was concentrated under vacuum. The oily residue was dissolved in ethyl acetate and the ethyl acetate was washed with aqueous sodium bicarbonate solution and then brine. After drying over sodium sulfate the ethyl acetate was concentrated under vacuum, giving a solid residue. This solid was recrystallized from dichloroethane to give 1.0 g of product; m.p. 103°–104.5°. $^1$H-NMR,δ (DMSO, d₆) 7.97 (2H, S); 7.75 (1H, d, J=3); 7.57 (1H, d, J=3); 4.00 (2H, t, J=6); 3.50 (2H, m); 1.90 (5H, m).

Anal. Calc'd. for $C_9H_{13}NO_6S_3$: C, 33.02; H, 4.00; N, 4.28. Found: C, 32.84; H, 3.96; N, 4.25.

EXAMPLE 14

5-(3-methoxyacetyloxypropanesulfonyl)thiophene-2-sulfonamide

To a solution of 5-(3-hydroxypropane sulfonyl)thiophene-2-sulfonamide (1.2 g, 4.2 mmol) in 75 ml of THF was added 0.4 ml of pyridine and 0.5 g of methoxyacetyl chloride. The reaction mixture was stirred for 18 hours at room temperature. The reaction mixture was filtered and the filtrate was concentrated under vacuum. The oily residue was dissolved in ethyl acetate and the ethyl acetate was washed with water and then brine. After drying over sodium sulfate the ethyl acetate was concentrated under vacuum, giving an oily residue. A crystalline product was obtained by dissolving the oil in hot dichloroethane and then cooling to 0° C. The yield was 0.8 g. m.p. 93°–95° C. $^1$H-NMR, δ (DMSO, $d_6$) 8.00 (2H, s); 7.80 (1H, d, J=3); 7.63 (1H, d, J=3); 4.12 (2H, t, J=6); 4.00 (2H, s); 3.55 (2H, m); 3.27 (3H, s); 1.91 (2H, m).

Anal. Calc'd. for $C_{10}H_{15}NO_7S_3$: C, 33.60; H, 4.23; N, 3.92. Found: C, 34.02; H, 4.26; N, 3.90.

Employing the procedure substantially as described in Examples 12 and 13 but using the acyl chlorides and 5-(hydroxyalkylsulfonyl)thiophene-2-sulfonamides described in Table V, there are produced the 5-(acyloxyalkylsulfonyl)thiophene-2-sulfonamides also described in Table V.

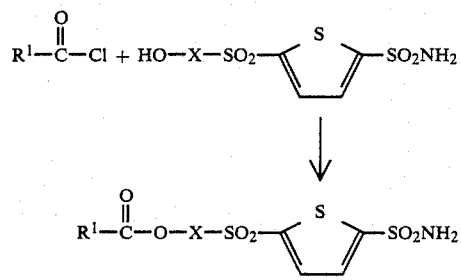

TABLE V

| $R^1$ | X |
| --- | --- |
| CH$_3$— | —CH$_2$CH$_2$— |
| CH$_3$O—CH$_2$— | —CH$_2$CH$_2$— |
| HOOC—CH$_2$CH$_2$— | cyclohexyl-CH$_2$— |
| HOOC—CH(NH$_2$)—CH$_2$CH$_2$— | thienyl— |
| phenyl | —CH$_2$CH$_2$CH$_2$— |
| pyridyl(N) | —CH$_2$CH$_2$CH$_2$— |

EXAMPLE 15

1-Hydroxy-3-(2-sulfamoylthiophene-5-sulfonyl)propane-1-sodium sulfate

A mixture of 3.00 g of 5-(3-hydroxypropylsulfonyl)thiophene-2-sulfonamide and 3.00 g of sulfamic acid in 20 ml of dry pyridine is refluxed gently for 36 hours. At the end of the reaction, the pyridine is distilled from the mixture under vacuum at 50° C. The residue is dissolved in water and made basic by addition of concentrated ammonia. The solvent is evaporated. The product is separated from residual ammonium sulfamate by extraction into ethanol. The ethanol extract is filtered and evaporated to give crude sulfate as the ammonium salt. The salt is dissolved in distilled water and titrated with 1 equivalent of sodium hydroxide. The solvent is evaporated leaving the crude sodium sulfate salt. The product is boiled with 40 ml of saturated sodium chloride solution and sufficient water is added to obtain a clear solution. Upon cooling, 2.00 g of a white solid separates.

Treating the ammonium salt produced in Example 15 with potassium hydroxide, tetramethylammonium hydroxide, pyridine, imidazole, pralidoxime hydroxide or thiamine in place of the sodium hydroxide used in Example 15 prepares the corresponding salts.

EXAMPLE 16

1-Hydroxy-3-(2-sulfamoylthiophene-5-sulfonyl)propane-1-disodium phosphate

A solution of 2.5 g of 5-(3-hydroxypropylsulfonyl)-thiophene-2-sulfonamide in 10 ml of pyridine is added over a 1 minute period to a well-stirred solution of 1.02 ml of phosphorous oxychloride in pyridine (10 ml) at 0° C. After 15 to 30 minutes the reaction mixture is poured into ice-water and the resulting solution is stirred for 15 minutes. The solvents were evaporated under high vacuum on a rotary evaporator. The product is resuspended in water and the pH of the solution is adjusted to 7.8±0.6. The solvents were removed and the solid dried under high vacuum. The solid is redissolved in 100 ml of distilled water. Gradual addition of 400 ml of acetone leads to precipitation of the title compound.

Mixed esters of the type:

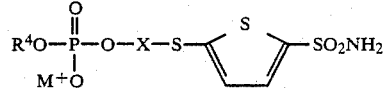

wherein $R^4$ is $C_{1-3}$alkyl or phenyl-$C_{1-3}$alkyl are prepared by reacting an hydroxy compound with an appropriate alkyldichlorophosphate; e.g. ethyldichlorophosphate, or benzyldichlorophosphate.

EXAMPLE 17

2-sulfamoylthiophene-5-(3-propyl) 2-Methylpropyl Carbonate

A solution of 2-sulfamoylthiophene-5-(3-propanol) (0.01 mole) in acetone (45 ml) at −5° is treated with triethylamine (1.21 g; 0.01 mole). Then a solution of isobutyl chloroformate (1.64 g; 0.012 mole) in acetone (5 ml) is added, dropwise, during 15 min. at −5° C.

After 15 minutes, the reaction mixture is poured into water (300 ml). The resulting semi-solid is extracted into ethyl acetate, washed with saturated sodium chloride solution and dried over sodium sulfate. Removal of solvent in vacuo provides the desired product.

Employing the procedure substantially as described in Example 17 but substituting for the thiophene used therein an equimolecular amount of the thiophenes and using isobutyl chloroformate as in Example 17 or substituting therefor the chloroformates described in Table VI, there are produced the carbonates also described in Table VI in accordance with the following reaction scheme:

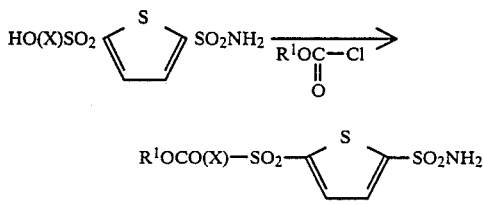

TABLE VI

| $R^1$ | X |
|---|---|
| $CH_3CH(CH_3)CH_2-$ | $-CH_2CH_2-$ |
| $CH_3CH(CH_3)CH_2-$ | benzyl $-CH_2-$ |
| $CH_3CH(CH_3)CH_2-$ | cyclohexyl |
| phenyl | $-(CH_2)_3-$ |
| $CH_3CH_2-$ | $-(CH_2)_2-$ |
| $CH_3(CH_2)_2-$ | $-CH_2-CH=CH-CH_2-$ |
| $(CH_3)_3C-$ | $-CHCH_2-$ $\;\;CH_3$ |
| $CH_3O(CH_2)_7-$ | $-CH_2CH_2-$ |
| phenyl | cyclopentyl |
| pyridyl | $-(CH_2)_3-$ |

EXAMPLE 18

| 5-(3-hydroxypropylsulfonyl) thiophene-2-sulfonamide (I) | 1 mg. | 15 mg. |
|---|---|---|
| Monobasic sodium phosphate .2H$_2$O | 9.38 mg. | 6.10 mg. |
| Dibasic sodium phosphate .12H$_2$O | 28.48 mg. | 16.80 mg. |
| Benzalkonium chloride | 0.10 mg. | 0.10 mg. |
| Water for injection q.s. ad. | 1.0 ml. | 1.0 ml. |

Compound I, phospate buffer salts, and benzalkonium chloride are added to and dissolved in water. The pH of the composition is adjusted to 6.8 and diluted to volume. The composition is rendered sterile by ionizing radiation.

EXAMPLE 19

| 5-(2-hydroxyethylsulfonyl) thiophene-2-sulfonamide (II) | 5 mg. |
|---|---|
| petrolatum q.s. ad. | 1 gram |

Compound II and the petrolatum are aseptically combined.

EXAMPLE 20

| 5-(3-hydroxypropylsulfonyl) thiophene-2-sulfonamide | 1 mg. |
|---|---|
| Hydroxypropylcellulose q.s. | 12 mg. |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

EXAMPLE 21

| 5-(3-hydroxypropylsulfonyl) thiophene-2-sulfonamide | 1 mg. |
|---|---|
| Hydroxypropyl cellulose q.s. ad. | 12 mg. |

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R. H. cabinet until it is pliable. Appropriately sized inserts are cut from the film.

EXAMPLE 22

| 5-(3-hydroxypropylsulfonyl)thiophene-2-sulfonamide | 1 mg. |
|---|---|
| Hydroxypropylmethyl cellulose q.s. ad. | 12 mg. |

Ophthalmic inserts are manufactured from a solvent cast film which is prepared by making a viscous solution of the powdered blend of the above ingredients using a methanol/water solvent system (10 ml. methanol is added to 2.5 g. of the powdered blend, to which 11 ml. of water (in three divided portions) is added. The solution is placed on a Teflon plate and allowed to dry at ambient conditions. After drying, the film is placed in an 88% R. H. cabinet until it is pliable. Appropriately sized inserts are then cut from the film.

EXAMPLE 23

| | |
|---|---|
| 5-(3-hydroxypropylsulfonyl)thiophene-2-sulfonamide | 1 mg. |
| Hydroxypropylmethyl cellulose q.s. ad. | 12 mg. |

Ophthalmic inserts are manufactured from compression molded films which are prepared on a Carver Press by subjecting the powdered mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R. H. at 30° C.) for two to four days. After removal from the humidity cabinet, the vials are stoppered and then capped. The vials containing the hydrated insert are then autoclaved at 250° F. for one-half hour.

It is highly preferred that the solid inserts of this invention are available for use by the patient in a pathogen free condition. Thus, it is preferred to sterilize the inserts and to insure against recontamination, the sterilization is preferably conducted after packaging. The best mode of sterilizing is to employ ionizing radiation including radiation emanating from Cobalt 60 or high energy electron beams.

What is claimed is:

1. A compound of structural formula:

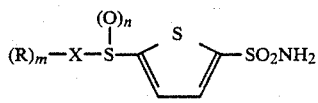

or a pharmaceutically acceptable salt thereof wherein
X is a straight or branched, saturated or unsaturated hydrocarbon, or a saturated cyclic hydrogen, of 1 to 10 carbon atoms;
m is 1 or 2;
n is 0, 1 or 2;
R is
(1) hydroxy

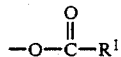
(2)

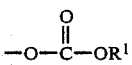
(3)

(4) —N($R^1$)$_2$ wherein the $R^1$ groups are the same or different, or can be joined toether to form, with the nitrogen atom to which they are attached, a 5- or 6- membered hetrocycle selected from piperidino, piperazino, morpholino and 1-pyrrolyl

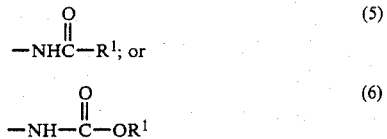

wherein $R^1$ is
(a) hydrogen,
(b) $C_{1-4}$alkyl,
(c) hydroxy-$C_{1-4}$alkyl,
(d) $C_{1-4}$alkoxy-$C_{1-4}$alkyl,
(e) phenyl,
(f) pridyl,
(g) carboxy-$C_{1-4}$alkyl,
(h) ω-amino-ω-carboxy-$C_{1-4}$ alkyl.

2. A compound of structural formula:

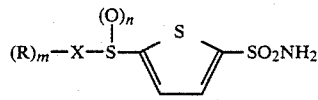

or a pharmaceutically acceptable salt thereof wherein
x is a straight or branched, saturate or unsaturated hydrocarbon, or a saturated cyclic hydrocarbon, of 1 to 10 carbon atoms;
m is 1 or 2;
n is 0, 1 or 2;
R is
(1) hydroxy

(2)

(3)

3. The compound of claim 2 wherein n is 0 or 2, and X —(CH$_2$)$_{1-4}$—.

4. The compound of claim 3 which is:
5-(2-hydroxyethylthio)thiophene-2-sulfonamide,
5-(2-hydroxyethylsulfonyl)thiophene-2-sulfonamide,
5-(2,3-dihydroxypropylthio)thiophene-2-sulfonamide,
5-(2,3-dihydroxypropylsulfonyl)thiophene-2-sulfonamide,
5-(3-hydroxypropylsulfonyl)thiophene-2-sulfonamide,
5-(3-hydroxypropylthio)thiophene-2-sulfonamide,
5-(3-methoxyacetyloxypropanesulfonyl)thiophene-2-sulfonamide,
5-(3-acetoxypropanesulfonyl)thiophene-2-sulfonamide, or
5-(trans-4-hydroxycyclohexylsulfonyl) thiophene-2-sulfonamide.

5. The compound of claim 4, which is:
5-(2-hydroxyethylsulfonyl)thiophene-2-sulfonamide, or
5-(2-hydroxypropylsulfonyl)thiophene-2-sulfonamide.

* * * * *